United States Patent
Qiu et al.

(10) Patent No.: US 7,765,234 B2
(45) Date of Patent: Jul. 27, 2010

(54) DATA FLOW MANAGEMENT IN GENERATING DIFFERENT SIGNAL FORMATS USED IN OPTICAL METROLOGY

(75) Inventors: Hong Qiu, Union City, CA (US); Junwei Bao, Palo Alto, CA (US); Wei Liu, Santa Clara, CA (US); Jeffrey Alexander Chard, Sunnyvale, CA (US); Miao Liu, Mountain View, CA (US); Gang He, Sunnyvale, CA (US); Hemalatha Erva, Fremont, CA (US); Vi Vuong, Fremont, CA (US)

(73) Assignee: Tokyo Electron Limited, Tokyo (JP)

( * ) Notice: Subject to any disclaimer, the term of this patent is extended or adjusted under 35 U.S.C. 154(b) by 958 days.

(21) Appl. No.: 11/580,716

(22) Filed: Oct. 12, 2006

(65) Prior Publication Data
US 2008/0089574 A1     Apr. 17, 2008

(51) Int. Cl.
*G06Q 50/00* (2006.01)
(52) U.S. Cl. .................. 707/793; 702/189; 356/399; 703/6; 382/141; 707/953
(58) Field of Classification Search ............... 707/793, 707/953
See application file for complete search history.

(56) References Cited

U.S. PATENT DOCUMENTS

| 6,785,638 B2 | 8/2004 | Niu et al. |
| 6,792,328 B2 | 9/2004 | Laughery et al. |

(Continued)

FOREIGN PATENT DOCUMENTS

WO    WO 02/23231 A2 *    3/2002

OTHER PUBLICATIONS

U.S. Appl. No. 11/580,570, filed Oct. 12, 2006 for Qiu et al.
Li, L. (1996). "Formulation and comparison of two recursive matrix algorithms for modeling layered diffraction gratings," *Journal of the Optical Society of America A* 13:1024-1035.

(Continued)

*Primary Examiner*—James Trujillo
*Assistant Examiner*—Albert Phillips
(74) *Attorney, Agent, or Firm*—Manuel B Madriaga

(57) ABSTRACT

To manage data flow in generating different signal formats for use in optical metrology, a project data object is created. A first option data object is created. The first option data object has a set of signal parameters. Different settings of the set of signal parameters correspond to different signal formats for diffraction signals. A version number is associated with the first option data object. The first option data object is linked with the project data object. At least a second option data object is created. The second option data object has a set of signal parameters. Different settings of the set of signal parameters correspond to different signal formats for diffraction signals. The set of signal parameters of the first option data object and the set of signal parameters of the second option data object are set differently. Another version number is associated with the second option data object. The second option data object is linked with the project data object. The project data object, the first option data object, and the second option data object are stored. The version numbers associated with the first option data object and the second option data object are stored. The link between the first option data object and the project data object is stored. The link between the second option data object and the project data object is stored.

26 Claims, 10 Drawing Sheets

U.S. PATENT DOCUMENTS

| | | |
|---|---|---|
| 6,891,626 B2 | 5/2005 | Niu et al. |
| 6,943,900 B2 | 9/2005 | Niu et al. |
| 7,064,829 B2 * | 6/2006 | Li et al. .................. 356/369 |
| 2004/0267397 A1 | 12/2004 | Doddi et al. |
| 2005/0057748 A1 * | 3/2005 | Vuong et al. ............ 356/237.5 |
| 2005/0209816 A1 | 9/2005 | Vuong et al. |
| 2005/0275850 A1 * | 12/2005 | Bischoff et al. ............ 356/600 |

OTHER PUBLICATIONS

Haykin, S. (1999). *Neural Networks*. 2nd edition, M. Horton ed., Prentice Hall: Upper Saddle River, New Jersey, 9 pages (Table of Contents).

Ausschnitt, C. P. (Feb. 23, 2004). "A New Approach to Pattern Metrology," *Proceedings of SPIE* 5375:51-65.

\* cited by examiner

DATA FLOW MANAGEMENT IN GENERATING DIFFERENT SIGNAL FORMATS USED IN OPTICAL METROLOGY

BACKGROUND

1. Field

The present application generally relates to optical metrology of a structure formed on a semiconductor wafer, and, more particularly, to data flow management in generating different signal formats used in optical metrology.

2. Description of the Related Art

Optical metrology involves directing an incident beam at a structure, measuring the resulting diffracted beam, and analyzing the diffracted beam to determine a feature of the structure. In semiconductor manufacturing, optical metrology is typically used for quality assurance. For example, after fabricating a structure on a semiconductor wafer, an optical metrology tool is used to determine the profile of the structure. By determining the profile of the structure, the quality of the fabrication process utilized to form the structure can be evaluated.

In one conventional optical metrology system, a diffraction signal collected from illuminating a structure (a measured diffraction signal) is compared to simulated diffraction signals, which are associated with hypothetical profiles of the structure. When a match is found between the measured diffraction signal and one of the simulated diffraction signals, the hypothetical profile associated with the matching simulated diffraction signal is presumed to represent the actual profile of the structure.

The hypothetical profiles, which are used to generate the simulated diffraction signals, are generated based on a profile model that characterizes the structure to be examined. Thus, in order to accurately determine the profile of the structure using optical metrology, a profile model that accurately characterizes the structure should be used. The process of generating a profile model can involve a large amount of data processing and analysis.

SUMMARY

In one exemplary embodiment, to manage data flow in generating different signal formats for use in optical metrology, a project data object is created. A first option data object is created. The first option data object has a set of signal parameters. Different settings of the set of signal parameters correspond to different signal formats for diffraction signals. A version number is associated with the first option data object. The first option data object is linked with the project data object. At least a second option data object is created. The second option data object has a set of signal parameters. Different settings of the set of signal parameters correspond to different signal formats for diffraction signals. The set of signal parameters of the first option data object and the set of signal parameters of the second option data object are set differently. Another version number is associated with the second option data object. The second option data object is linked with the project data object. The project data object, the first option data object, and the second option data object are stored. The version numbers associated with the first option data object and the second option data object are stored. The link between the first option data object and the project data object is stored. The link between the second option data object and the project data object is stored.

DESCRIPTION OF THE DRAWING FIGURES

Figure 5A:
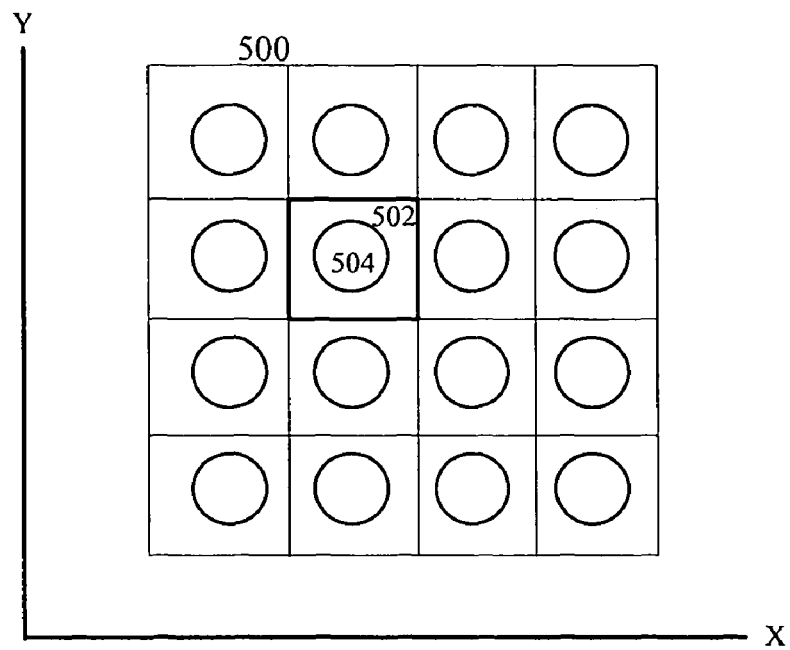
Figure 5B:
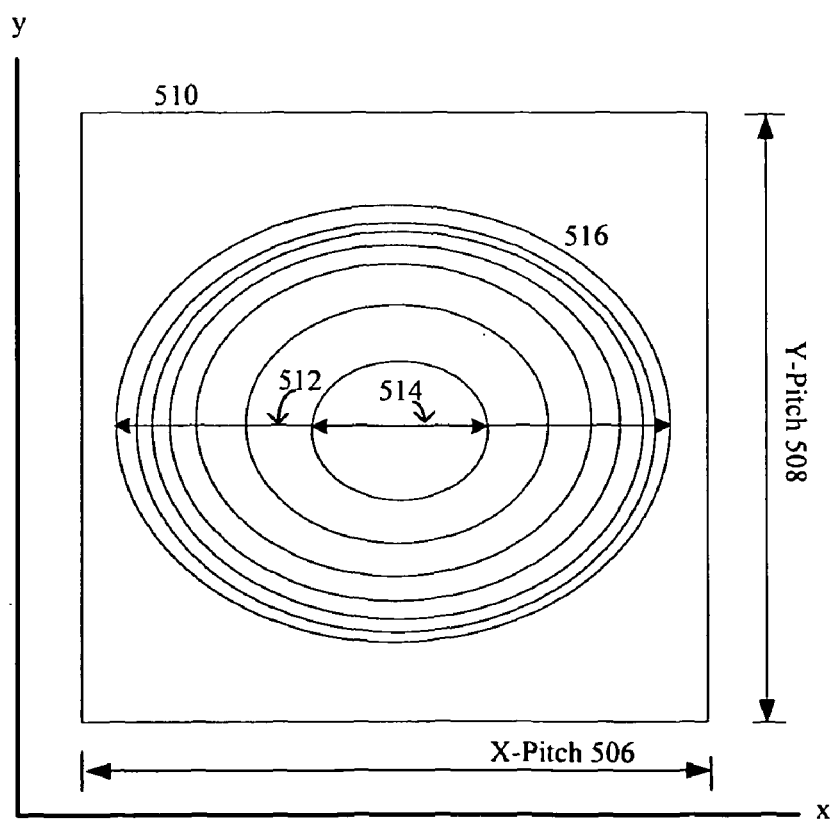
Figure 5C:
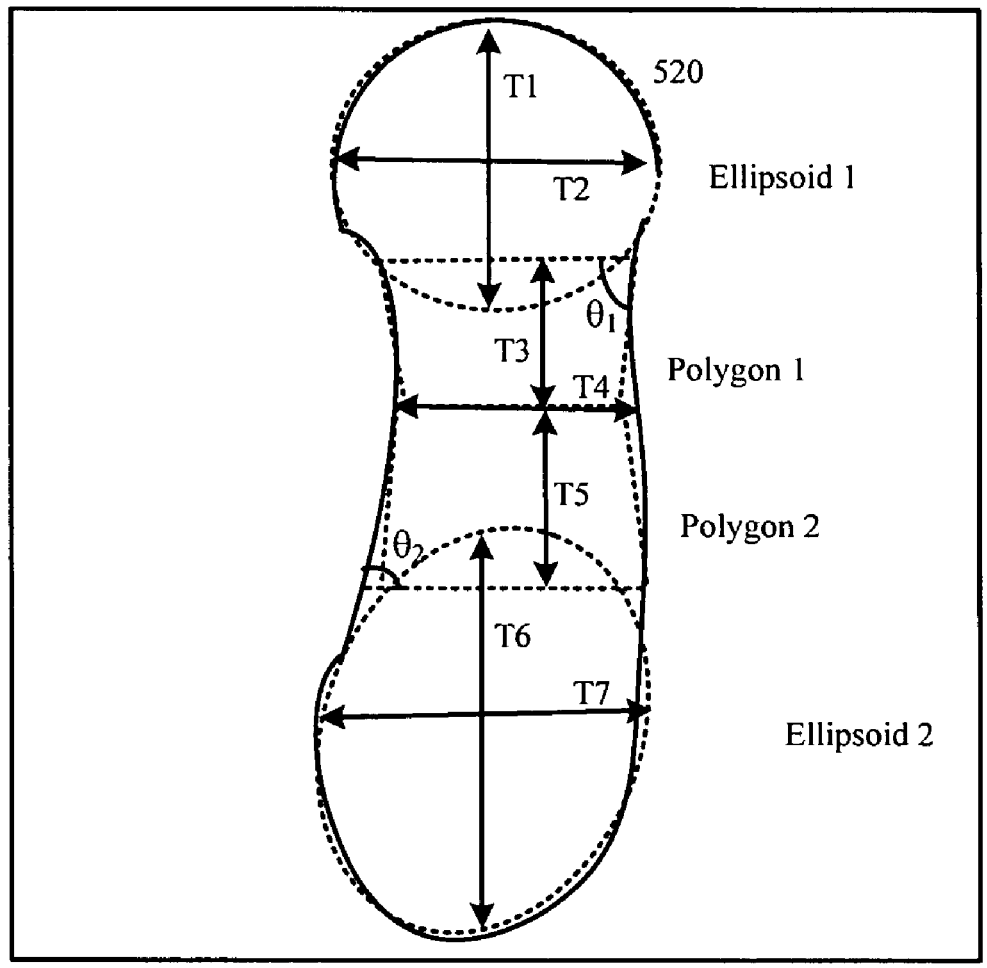
Figure 6:
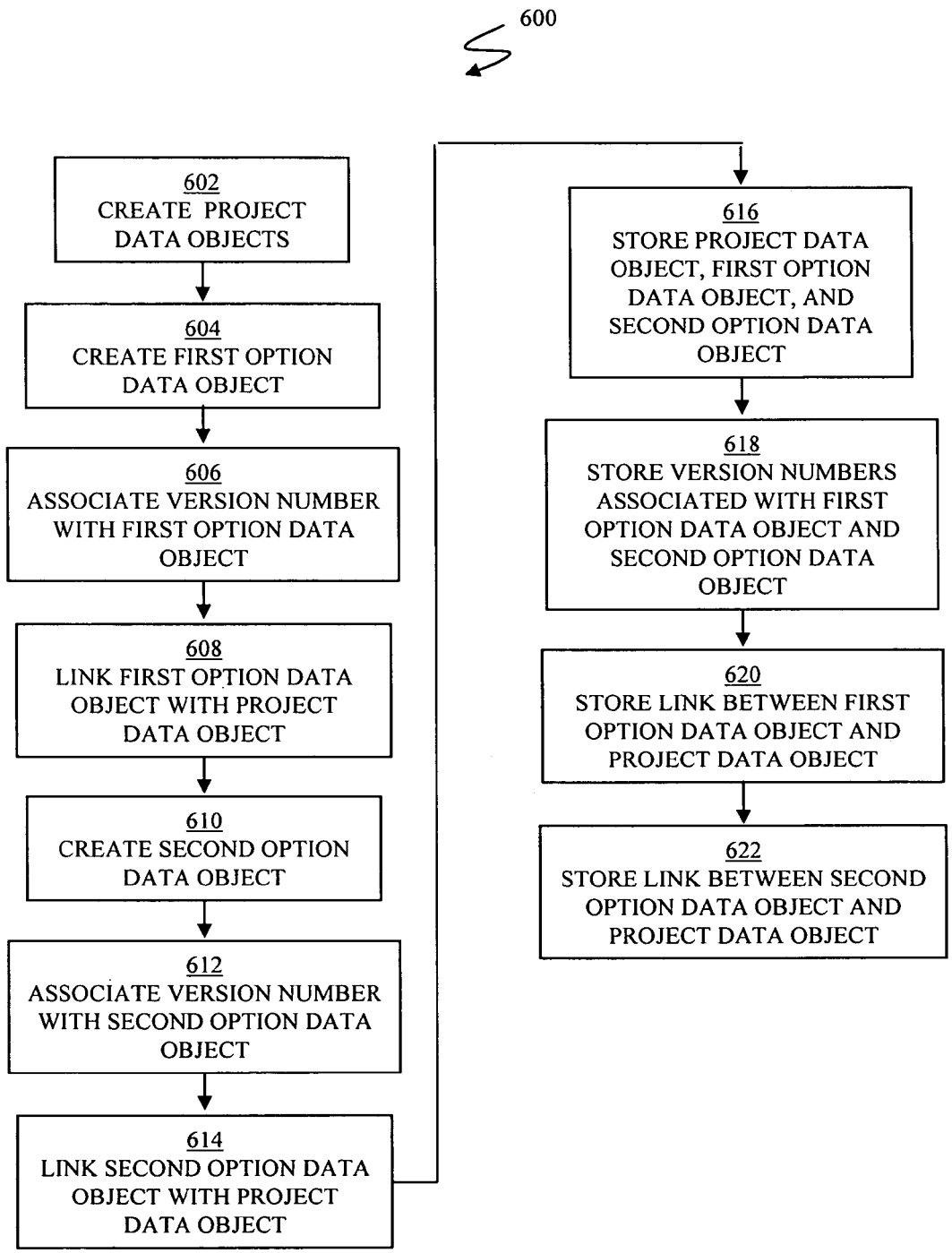
Figure 7:
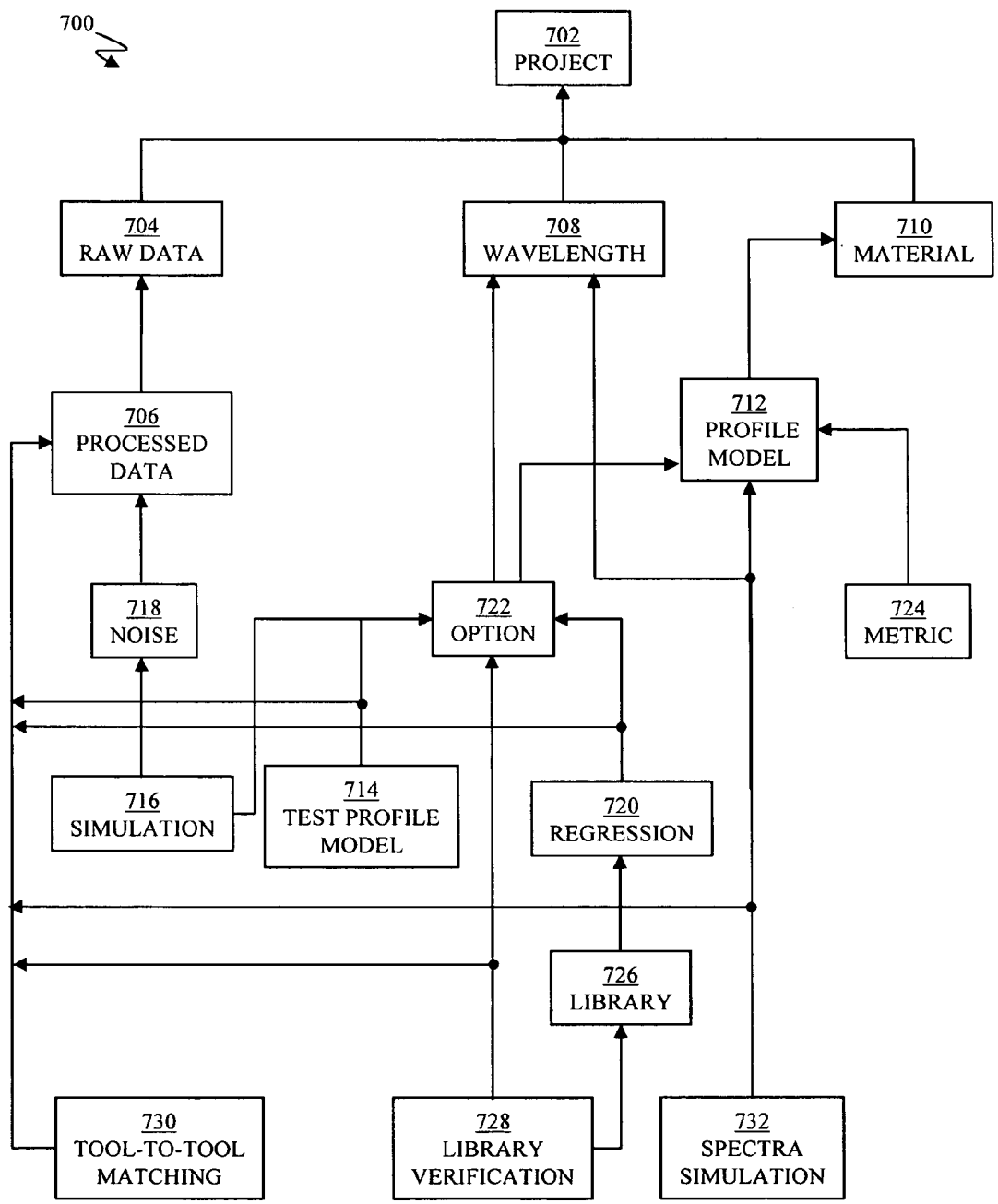
Figure 8:
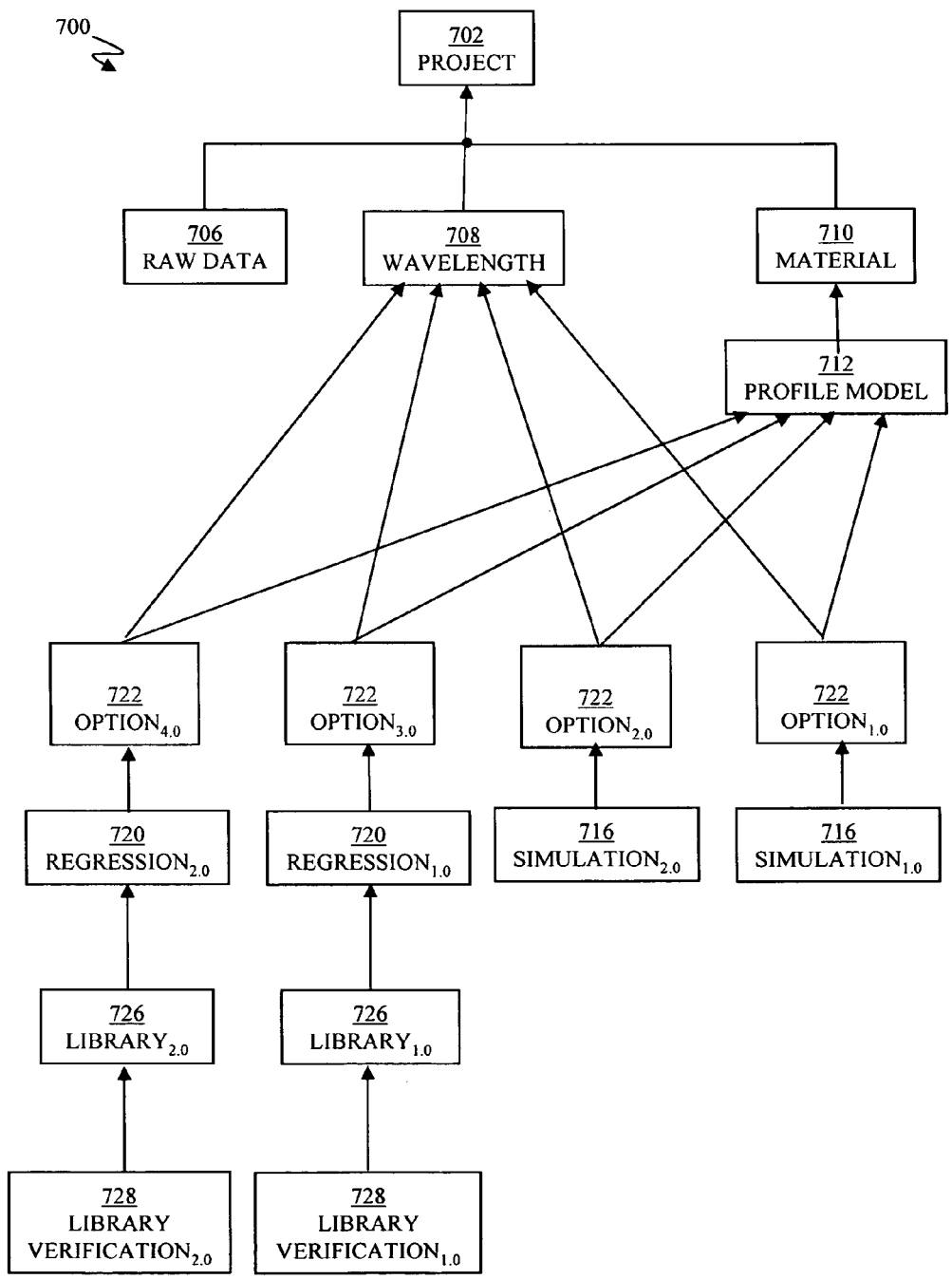
Figure 9:
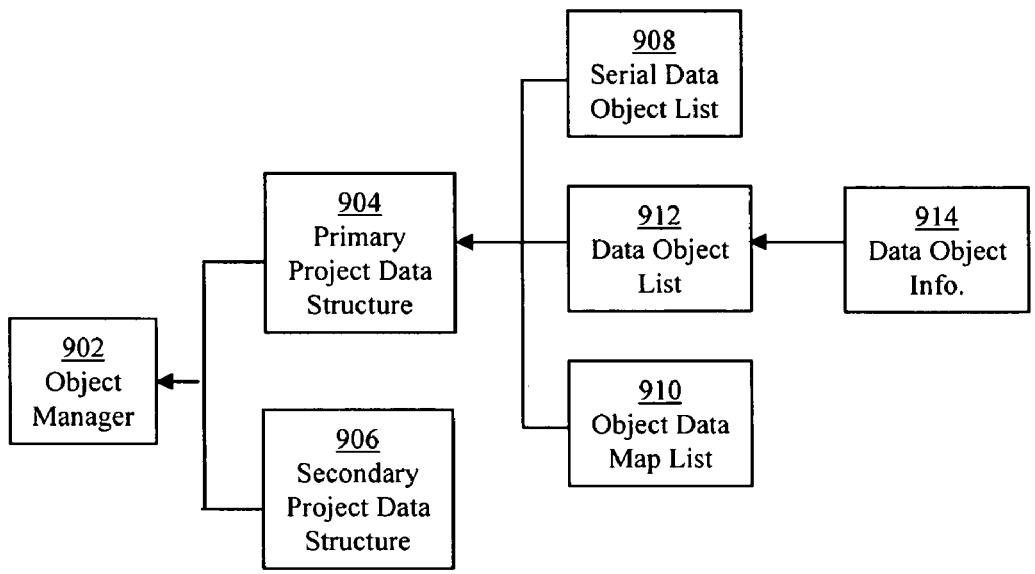
Figure 10:
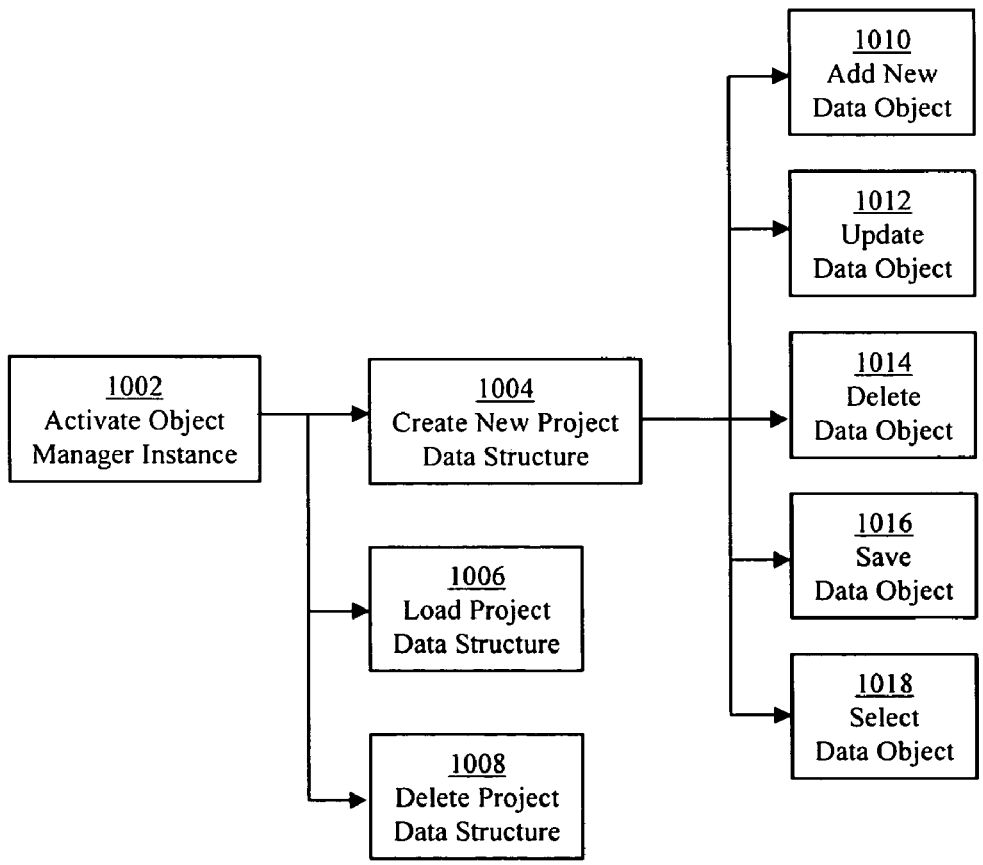

FIGS. 5A, 5B, and 5C depict characterization of two-dimension repeating structures;

FIG. 6 depicts an exemplary process of managing data flow in generating processing options;

FIGS. 7 and 8 depict an exemplary project data structure;

FIG. 9 depicts an exemplary class diagram used to store an exemplary project data structure;

FIG. 10 depicts exemplary operations performed by an object manager; and

Figure 11:
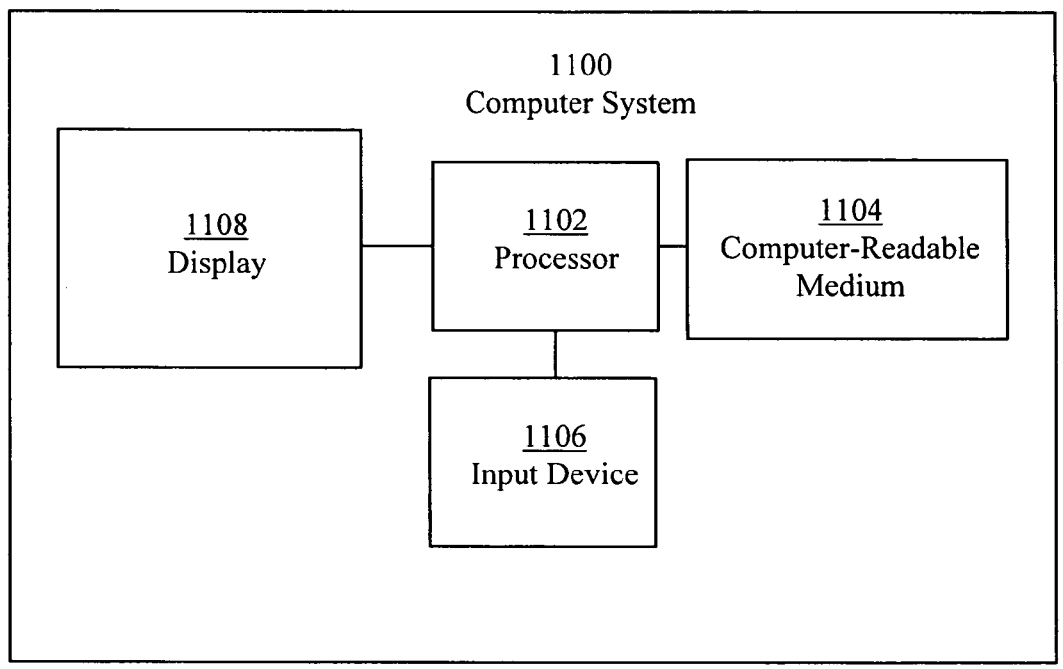

FIG. 11 depicts an exemplary computer system.

DETAILED DESCRIPTION

The following description sets forth numerous specific configurations, parameters, and the like. It should be recognized, however, that such description is not intended as a limitation on the scope of the present invention, but is instead provided as a description of exemplary embodiments.

1. Optical Metrology Tools

Figure 1:
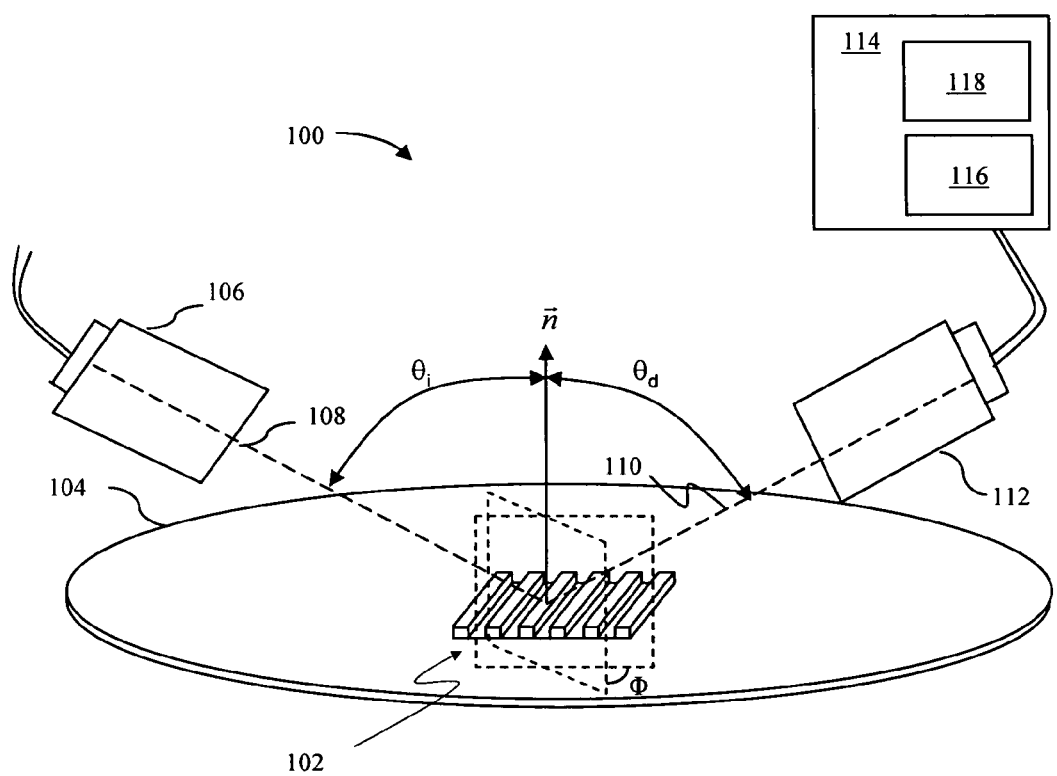
FIG. 1 depicts an exemplary optical metrology system.

With reference to FIG. 1, an optical metrology system 100 can be used to examine and analyze a structure formed on a semiconductor wafer 104. For example, optical metrology system 100 can be used to determine one or more features of a periodic grating 102 formed on wafer 104. Periodic grating 102 can be formed in a test pad on wafer 104, such as adjacent to a die formed on wafer 104. Periodic grating 102 can be formed in a scribe line and/or an area of the die that does not interfere with the operation of the die.

As depicted in FIG. 1, optical metrology system 100 can include a photometric device with a source 106 and a detector 112. Periodic grating 102 is illuminated by an incident beam 108 from source 106. The incident beam 108 is directed onto periodic grating 102 at an angle of incidence $\theta_i$ with respect to normal $\vec{n}$ of periodic grating 102 and an azimuth angle $\Phi$ (i.e., the angle between the plane of incidence beam 108 and the direction of the periodicity of periodic grating 102). Diffracted beam 110 leaves at an angle of $\theta_d$ with respect to normal and is received by detector 112. Detector 112 converts the diffracted beam 110 into a measured diffraction signal, which can include reflectance, tan($\Psi$), cos($\Delta$), Fourier coefficients, and the like. Although a zero-order diffraction signal is depicted in FIG. 1, it should be recognized that non-zero orders can also be used. For example, see Ausschnitt, Christopher P., "A New Approach to Pattern Metrology," Proc. SPIE 5375-7, Feb. 23, 2004, pp 1-15, which is incorporated herein by reference in its entirety.

Optical metrology system 100 also includes a processing module 114 configured to receive the measured diffraction signal and analyze the measured diffraction signal. The processing module is configured to determine one or more features of the periodic grating using any number of methods which provide a best matching diffraction signal to the measured diffraction signal. These methods, which are described below, include a library-based process, or a regression based process using simulated diffraction signals obtained by rigorous coupled wave analysis and machine learning systems.

2. Library-based Process of Determining Feature of Structure

In a library-based process of determining one or more features of a structure, the measured diffraction signal is compared to a library of simulated diffraction signals. More specifically, each simulated diffraction signal in the library is associated with a hypothetical profile of the structure. When a match is made between the measured diffraction signal and one of the simulated diffraction signals in the library or when the difference of the measured diffraction signal and one of the simulated diffraction signals is within a preset or matching criterion, the hypothetical profile associated with the matching simulated diffraction signal is presumed to represent the actual profile of the structure. The matching simulated diffraction signal and/or hypothetical profile can then be utilized to determine whether the structure has been fabricated according to specifications.

Thus, with reference again to FIG. 1, in one exemplary embodiment, after obtaining a measured diffraction signal, processing module 114 then compares the measured diffraction signal to simulated diffraction signals stored in a library 116. Each simulated diffraction signal in library 116 can be associated with a hypothetical profile. Thus, when a match is made between the measured diffraction signal and one of the simulated diffraction signals in library 116, the hypothetical profile associated with the matching simulated diffraction signal can be presumed to represent the actual profile of periodic grating 102.

The set of hypothetical profiles stored in library 116 can be generated by characterizing the profile of periodic grating 102 using a profile model. The profile model is characterized using a set of profile parameters. The profile parameters in the set are varied to generate hypothetical profiles of varying shapes and dimensions. The process of characterizing the actual profile of periodic grating 102 using profile model and a set of profile parameters can be referred to as parameterizing.

Figure 2A:
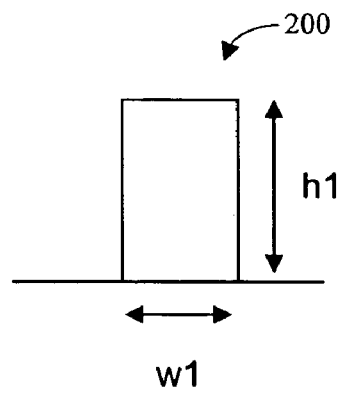
FIGS. 2A-2E depict exemplary profile models.
Figure 2C:
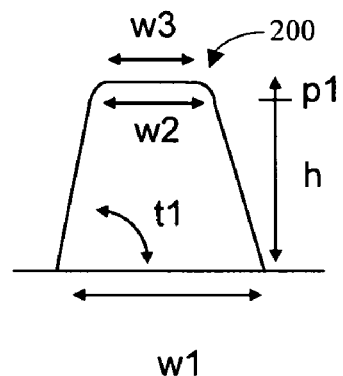
Figure 2B:
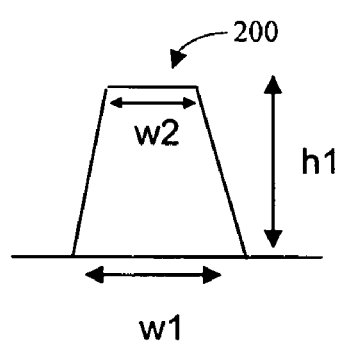
Figure 2D:
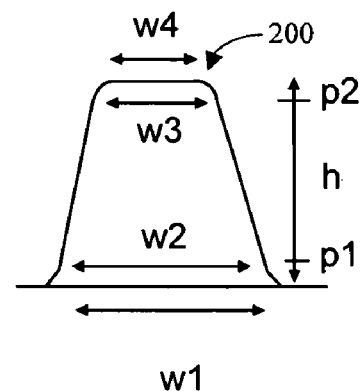
Figure 2E:
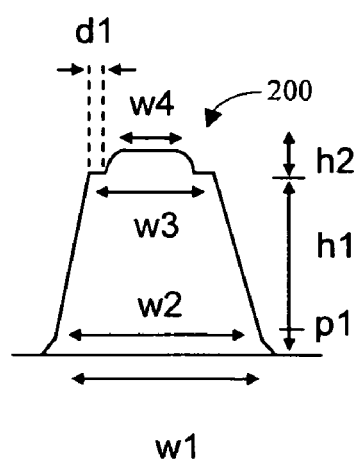

For example, as depicted in FIG. 2A, assume that profile model 200 can be characterized by profile parameters h1 and w1 that define its height and width, respectively. As depicted in FIGS. 2B to 2E, additional shapes and features of profile model 200 can be characterized by increasing the number of profile parameters. For example, as depicted in FIG. 2B, profile model 200 can be characterized by profile parameters h1, w1, and w2 that define its height, bottom width, and top width, respectively. Note that the width of profile model 200 can be referred to as the critical dimension (CD). For example, in FIG. 2B, profile parameter w1 and w2 can be described as defining the bottom CD (BCD) and top CD (TCD), respectively, of profile model 200.

As described above, the set of hypothetical profiles stored in library 116 (FIG. 1) can be generated by varying the profile parameters that characterize the profile model. For example, with reference to FIG. 2B, by varying profile parameters h1, w1, and w2, hypothetical profiles of varying shapes and dimensions can be generated. Note that one, two, or all three profile parameters can be varied relative to one another.

With reference again to FIG. 1, the number of hypothetical profiles and corresponding simulated diffraction signals in the set of hypothetical profiles and simulated diffraction signals stored in library 116 (i.e., the resolution and/or range of library 116) depends, in part, on the range over which the set of profile parameters and the increment at which the set of profile parameters is varied. The hypothetical profiles and the simulated diffraction signals stored in library 116 are generated prior to obtaining a measured diffraction signal from an actual structure. Thus, the range and increment (i.e., the range and resolution) used in generating library 116 can be selected based on familiarity with the fabrication process for a structure and what the range of variance is likely to be. The range and/or resolution of library 116 can also be selected based on empirical measures, such as measurements using AFM, X-SEM, and the like.

For a more detailed description of a library-based process, see U.S. Pat. No. 6,943,900, titled GENERATION OF A LIBRARY OF PERIODIC GRATING DIFFRACTION SIGNALS, filed on Jul. 16, 2001, issued Sep. 13, 2005, which is incorporated herein by reference in its entirety.

3. Regression-based Process of Determining Feature of Structure

In a regression-based process of determining one or more features of a structure, the measured diffraction signal is compared to a simulated diffraction signal (i.e., a trial diffraction signal). The simulated diffraction signal is generated prior to the comparison using a set of profile parameters (i.e., trial profile parameters) for a hypothetical profile. If the measured diffraction signal and the simulated diffraction signal do not match or when the difference of the measured diffraction signal and one of the simulated diffraction signals is not within a preset or matching criterion, another simulated diffraction signal is generated using another set of profile parameters for another hypothetical profile, then the measured diffraction signal and the newly generated simulated diffraction signal are compared. When the measured diffraction signal and the simulated diffraction signal match or when the difference of the measured diffraction signal and one of the simulated diffraction signals is within a preset or matching criterion, the hypothetical profile associated with the matching simulated diffraction signal is presumed to represent the actual profile of the structure. The matching simulated diffraction signal and/or hypothetical profile can then be utilized to determine whether the structure has been fabricated according to specifications.

Thus, with reference again to FIG. 1, the processing module 114 can generate a simulated diffraction signal for a hypothetical profile, and then compare the measured diffraction signal to the simulated diffraction signal. As described above, if the measured diffraction signal and the simulated diffraction signal do not match or when the difference of the measured diffraction signal and one of the simulated diffraction signals is not within a preset or matching criterion, then processing module 114 can iteratively generate another simulated diffraction signal for another hypothetical profile. The subsequently generated simulated diffraction signal can be generated using an optimization algorithm, such as global optimization techniques, which includes simulated annealing, and local optimization techniques, which includes steepest descent algorithm.

The simulated diffraction signals and hypothetical profiles can be stored in a library 116 (i.e., a dynamic library). The simulated diffraction signals and hypothetical profiles stored in library 116 can then be subsequently used in matching the measured diffraction signal.

For a more detailed description of a regression-based process, see U.S. Pat. No. 6,785,638, titled METHOD AND SYSTEM OF DYNAMIC LEARNING THROUGH A REGRESSION-BASED LIBRARY GENERATION PROCESS, filed on Aug. 6, 2001, issued Aug. 31, 2004, which is incorporated herein by reference in its entirety.

4. Rigorous Coupled Wave Analysis

As described above, simulated diffraction signals are generated to be compared to measured diffraction signals. As will be described below, the simulated diffraction signals can be generated by applying Maxwell's equations and using a numerical analysis technique to solve Maxwell's equations. It should be noted, however, that various numerical analysis techniques, including variations of rigorous coupled wave analysis (RCWA), can be used.

In general, RCWA involves dividing a hypothetical profile into a number of sections, slices, or slabs (hereafter simply referred to as sections). For each section of the hypothetical profile, a system of coupled differential equations is generated using a Fourier expansion of Maxwell's equations (i.e., the components of the electromagnetic field and permittivity ($\epsilon$)). The system of differential equations is then solved using a diagonalization procedure that involves eigenvalue and eigenvector decomposition (i.e., Eigen-decomposition) of the characteristic matrix of the related differential equation system. Finally, the solutions for each section of the hypothetical profile are coupled using a recursive-coupling schema, such as a scattering matrix approach. For a description of a scattering matrix approach, see Lifeng Li, "Formulation and comparison of two recursive matrix algorithms for modeling layered diffraction gratings," J. Opt. Soc. Am. A13, pp 1024-1035 (1996), which is incorporated herein by reference in its entirety. For a more detail description of RCWA, see U.S. Pat. No. 6,891,626, titled CACHING OF INTRA-LAYER CALCULATIONS FOR RAPID RIGOROUS COUPLED-WAVE ANALYSES, filed on Jan. 25, 2001, issued May 10, 2005, which is incorporated herein by reference in its entirety.

5. Machine Learning Systems

The simulated diffraction signals can be generated using a machine learning system (MLS) employing a machine learning algorithm, such as back-propagation, radial basis function, support vector, kernel regression, and the like. For a more detailed description of machine learning systems and algorithms, see "Neural Networks" by Simon Haykin, Prentice Hall, 1999, which is incorporated herein by reference in its entirety. See also U.S. patent application Ser. No. 10/608, 300, titled OPTICAL METROLOGY OF STRUCTURES FORMED ON SEMICONDUCTOR WAFERS USING MACHINE LEARNING SYSTEMS, filed on Jun. 27, 2003, which is incorporated herein by reference in its entirety.

In one exemplary embodiment, the simulated diffraction signals in a library of diffraction signals, such as library 116 (FIG. 1), used in a library-based process are generated using a MLS. For example, a set of hypothetical profiles can be provided as inputs to the MLS to produce a set of simulated diffraction signals as outputs from the MLS. The set of hypothetical profiles and set of simulated diffraction signals are stored in the library.

In another exemplary embodiment, the simulated diffractions used in regression-based process are generated using a MLS, such as MLS 118 (FIG. 1). For example, an initial hypothetical profile can be provided as an input to the MLS to produce an initial simulated diffraction signal as an output from the MLS. If the initial simulated diffraction signal does not match the measured diffraction signal, another hypothetical profile can be provided as an additional input to the MLS to produce another simulated diffraction signal.

FIG. 1 depicts processing module 114 having both a library 116 and MLS 118. It should be recognized, however, that processing module 114 can have either library 116 or MLS 118 rather than both. For example, if processing module 114 only uses a library-based process, MLS 118 can be omitted. Alternatively, if processing module 114 only uses a regression-based process, library 116 can be omitted. Note, however, a regression-based process can include storing hypothetical profiles and simulated diffraction signals generated during the regression process in a library, such as library 116.

6. One Dimension Profiles and Two Dimension Profiles

Figure 3:
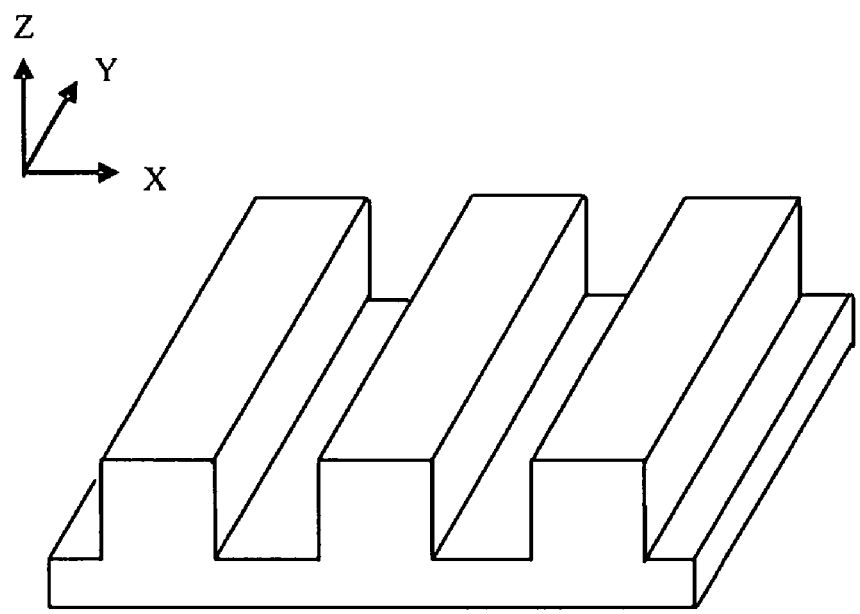
FIG. 3 depicts an exemplary profile that varies only in one dimension.

The term "one-dimension structure" is used herein to refer to a structure having a profile that varies only in one dimension. For example, FIG. 3 depicts a periodic grating having a profile that varies in one dimension (i.e., the x-direction). The profile of the periodic grating depicted in FIG. 3 varies in the z-direction as a function of the x-direction. However, the profile of the periodic grating depicted in FIG. 3 is assumed to be substantially uniform or continuous in the y-direction.

Figure 4:
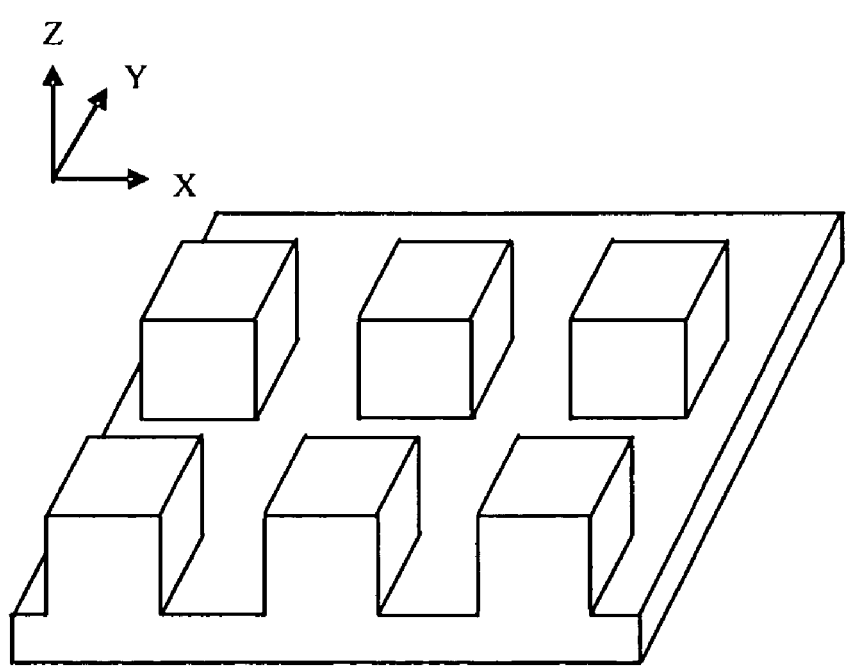
FIG. 4 depicts an exemplary profile that varies in two dimensions.

The term "two-dimension structure" is used herein to refer to a structure having a profile that varies in at least two-dimensions. For example, FIG. 4 depicts a periodic grating having a profile that varies in two dimensions (i.e., the x-direction and the y-direction). The profile of the periodic grating depicted in FIG. 4 varies in the y-direction.

Discussion for FIGS. 5A, 5B, and 5C below describe the characterization of two-dimension repeating structures for optical metrology modeling. FIG. 5A depicts a top-view of exemplary orthogonal grid of unit cells of a two-dimension repeating structure. A hypothetical grid of lines is superimposed on the top-view of the repeating structure where the lines of the grid are drawn along the direction of periodicity. The hypothetical grid of lines forms areas referred to as unit cells. The unit cells may be arranged in an orthogonal or non-orthogonal configuration. Two-dimension repeating structures may comprise features such as repeating posts, contact holes, vias, islands, or combinations of two or more shapes within a unit cell. Furthermore, the features may have a variety of shapes and may be concave or convex features or a combination of concave and convex features. Referring to FIG. 5A, the repeating structure 500 comprises unit cells with holes arranged in an orthogonal manner. Unit cell 502 includes all the features and components inside the unit cell 502, primarily comprising a hole 504 substantially in the center of the unit cell 502.

FIG. 5B depicts a top-view of a two-dimension repeating structure. Unit cell 510 includes a concave elliptical hole. FIG. 5B shows a unit cell 510 with a feature 516 that comprises an elliptical hole wherein the dimensions become progressively smaller until the bottom of the hole. Profile parameters used to characterize the structure includes the X-pitch 506 and the Y-pitch 508. In addition, the major axis of the ellipse 512 that represents the top of the feature 516 and the major axis of the ellipse 514 that represents the bottom of the feature 516 may be used to characterize the feature 516. Furthermore, any intermediate major axis between the top and bottom of the feature may also be used as well as any minor axis of the top, intermediate, or bottom ellipse, (not shown).

FIG. 5C is an exemplary technique for characterizing the top-view of a two-dimension repeating structure. A unit cell 518 of a repeating structure is a feature 520, an island with a peanut-shape viewed from the top. One modeling approach includes approximating the feature 520 with a variable number or combinations of ellipses and polygons. Assume further that after analyzing the variability of the top-view shape of the feature 520, it was determined that two ellipses, Ellipsoid 1 and Ellipsoid 2, and two polygons, Polygon 1 and Polygon 2 were found to fully characterize feature 520. In turn, parameters needed to characterize the two ellipses and two polygons comprise nine parameters as follows: T1 and T2 for Ellipsoid 1; T3, T4, and θ₁ for Polygon 1; T4, T5, and θ₂ for Polygon 2; T6 and T7 for Ellipsoid 2. Many other combinations of shapes could be used to characterize the top-view of the feature 520 in unit cell 518. For a detailed description of modeling two-dimension repeating structures, refer to U.S. patent application Ser. No. 11/061,303, OPTICAL METROLOGY OPTIMIZATION FOR REPETITIVE STRUCTURES, by Vuong, et al., filed on Apr. 27, 2004, which is incorporated in its entirety herein by reference.

7. Generating Metrology Data Objects and Linkages

As described above, in both a library-based process and a regression-based process, a simulated diffraction signal is generated based on a hypothetical profile of the structure to be examined. As also described above, the hypothetical profile is generated based on a profile model that characterizes the structure to be examined. The profile model is characterized using a set of profile parameters. The profile parameters of the set of profile parameters are varied to generate hypothetical profiles of varying shapes and sizes.

With reference to FIG. 6, an exemplary process 600 is depicted of managing the data flow associated with generating different signal formats for use in optical metrology. As described above, the generated profile models can be used to generate hypothetical profiles in a library-based process or a regression-based process of determining features of a structure. It should be recognized, however, that exemplary process 600 can be used to generate different signal formats at various times and for various reasons.

In step 602, a project data object is created. The project data object is associated with a project for which the different signal formats are being generated. For example, the project data object can be associated with particular hardware, recipe, and the like, to be used in forming and/or examining the structure to be examined. The project data object can include various information identifying the project to which it is associated, such as the name of the project, location, vendor, customer, and the like.

In step 604, a first option data object is created. The first option data object includes a set of signal parameters used to process diffraction signals. Different settings of the set of signal parameters correspond to different signal formats for the measured and/or simulated diffraction signals. In step 606, a version number is associated with the first option data object. In step 608, the first option data object is linked with the project data object created in step 602.

In step 610, a second option data object is created. The second option data object a set of signal parameters used to process diffraction signals. The set of signal parameters of the first option data object and the set of signal parameters of the second option data object are set differently. In step 612, another version number is associated with the second option data object. In step 614, the second option data object is linked with the project data object created in step 602.

In step 616, the project data object, the first option data object, and the second option data object are stored. In step 618, the version numbers associated with the first option data object and the second option data object are stored. In step 620, the link between the first option data object and the project data object is stored. In step 622, the link between the second option data object and the project data object is stored. It should be recognized that steps 616, 618, 620, and 622 can be performed separately or together.

As described above, in process 600, for a particular project data object, multiple option data objects can be created and linked with the project data object. Additionally, version numbers can be associated with the multiple option data objects. As also described above, the multiple option data objects are saved with the links to the project data object and the version numbers. Thus, a user can retrieve a project, which is associated with a project data object, and have access to multiple versions of option data objects linked to the project data object.

It should be recognized that the option data object need not be directly linked to the project data object. In one exemplary embodiment, a wavelength data object is created and linked between the project data object and the option data objects. Thus, the first and second option data objects described above are directly linked to the wavelength data object, which is in turn directly linked to the project data object.

The wavelength data object includes the range of wavelengths used in the optical metrology tool for the project. In one embodiment, the wavelength range and resolution or increment used in the optical metrology tool is specified. For example, the range of wavelengths used may be 200 to 800 nm. In another embodiment, the range and the resolution, i.e., the distance between points where measurements are made, is also specified. To illustrate the example, the project data object may specify a reflectometer and the wavelength data object may be 200 to 750 nm and a resolution of 10 nm. It is understood that the wavelength data object may include a set of selected wavelengths rather than a range. Alternatively, the range of wavelengths may be expressed as a range of electromagnetic energy and the like.

With reference to FIG. 7, an exemplary project data structure 700 is depicted. Project data structure 700 can be used to manage the data flow associated with generating different signal formats for use in optical metrology, such as exemplary process 600 depicted in FIG. 6 and described above.

In one exemplary embodiment, in project data structure 700, various types of data objects are linked together in a hierarchy. Thus, in the present exemplary embodiment, changes to data objects higher in the hierarchy of project data structure 700 result in changes to linked data objects lower in the hierarchy. Changes to data objects lower in the hierarchy of project data structure 700, however, do not necessarily result in changes to linked data objects higher in the hierarchy.

For example, a first level of project data structure 700 includes a project data object 702. A second level of project data structure 700 includes a raw-data data object 704 linked to project data object 702. As described above, project data object 702 can include various information identifying the project associated with project data object 702. Raw-data data object 704 includes measurements obtained using one or more optical metrology tools. As depicted in FIG. 7, raw-data data object 704 is lower than project data object 702 in the hierarchy of project data structure 700. Thus, changes to project data object 702 result in changes to raw-data data object 704. For example, if the project associated with project data object 702 is changed, then the one or more optical metrology tools associated with raw-data data object 704 are also changed. However, changes to raw-data data object 704 do not necessarily result in changes to project data object 702. For example, if the one or more optical metrology tools associated with raw-data data object 704 are changed, then the project associated with project data object 702 is not necessarily changed.

Wavelength data object 708 is linked to project data object 702. As described above, wavelength data object 708 can include the wavelengths to be used in examining the structure to be examined in the project associated with project data object 702. In particular, wavelengths data object 708 can include the wavelengths used by the one or more optical metrology tools to be used to examine the structure in the project associated with project data object 702. Thus, if the project associated with project data object 702 is changed, then the wavelengths in wavelength data object 708 are changed. However, if the wavelengths in wavelengths data object 708 are changed, then the project associated with project data object 702 is not necessarily changed.

Material data object 710 is linked to project data object 702. Material data object 710 includes data related to the materials of the structure to be examined in the project associated with project data object 702. For example, material data object 710 can include optical constants n (refractive index) & k (extinction coefficient).

A third level of the hierarchy of project data structure 700 includes a processed-data data object 706 linked to raw-data object 704. Processed-data data object 706 includes adjusted measurements obtained from one or more optical metrology tools. For example, the measurements in raw-data data object 704 can be adjusted and stored as processed-data data object 706. Thus, if raw-data data object 704 is changed, processed-data data object 706 is changed. However, if processed-data data object 706 is changed, raw-data data object 704 is not necessarily changed.

Profile model data object 712 is linked to material data object 710. Profile model data object 712 is associated with a profile model of the structure to be examined. As described above, the profile model is defined using profile parameters. Thus, profile model data object 712 includes the profile parameters that define the profile model.

A fourth level of the hierarchy of project data structure 700 includes a noise data object 718 linked to processed-data data object 706. Noise data object 718 includes data related to noise in measurements obtained from an optical metrology tool. Thus, the noise date in noise data object 718 can be used to obtain the adjusted measurements stored in processed-data object 706. In particular, measurements can be obtained from an optical metrology tool and stored in raw-data data object 704. Noise data related to the optical metrology tool in noise data object 718 can be used to adjust the measurements stored in raw-data data object 704. The adjusted measurements can be stored in processed-data data object 706.

Option data object 722 is linked to profile model data object 712 and wavelength data object 708. Diffraction signals from different types, brands, and/or models of optical metrology tools can be in various signal formats. Thus, in one exemplary embodiment, option data object 722 includes a set of signal parameters that can be used to process diffraction signals associated with different types, brands, and/or models of optical metrology tools. Different settings of the set of signal parameters correspond to different formats for the measured and/or simulated diffraction signals.

For example, assume option data object 722 includes a first signal parameter, P0, a second signal parameter P1, and a third signal parameter P2. In the present example, assume that each signal parameter can be set to be ON or OFF. Also assume that when one signal parameter is set to be ON, the remaining signal parameters are set to be OFF. Thus, in the present example, there are three possible settings for the signal parameters. In a first setting, the first signal parameter P0 is set to be ON and second and third signal parameters P1 and P2 are set to be OFF. In a second setting, second signal parameter P1 is set to be ON and first and third signal parameters P0 and P2 are set to be OFF. In a third setting, the third signal parameter P2 is set to be ON and first and second signal parameters P0 and P1 are set to be OFF.

Assume that when the set of signal parameters is set to the first setting, measured and/or simulated diffraction signals are processed by calculating average reflectivity ($R_s$ and $R_p$), where $R_s$ and $R_p$ are reflectivity in the s and p directions of polarization, respectively. Thus, when the set of signal parameters is set to the first setting, in the regression corresponding to regression data object 720, which is linked to option data object 722, the average reflectivity ($R_s$ and $R_p$) of the measured diffraction signal and the one or more simulated diffraction signals are calculated and compared. In the present example, the first setting of the set of signal parameters can correspond to a polarized reflectometer. Thus, the measured diffraction signal used in the regression previously described is obtained using a polarized reflectometer.

Assume that when the set of signal parameters is set to the second setting, measured and/or simulated diffraction signals are processed by calculating the average of the difference of the s and p reflectivity ($R_s-R_p$)/2. Thus, when the set of signal parameters is set to the second setting, in the regression corresponding to regression data object 720, which is linked to option data object 722, the average of the difference of the s and p reflectivity ($R_s-R_p$)/2 of the measured diffraction signal and the one or more simulated diffraction signals are calculated and compared. In the present example, the second setting of the set of signal parameters can correspond to a different type, brand, and/or model of a polarized reflectometer than the one corresponding to the first setting.

Assume that when the set of signal parameters is set to the third setting, measured and/or simulated diffraction signals are processed by calculating a combination of R, NSC. R is the reflectance parameter, N characterizes the difference between the square of the absolute value of the complex reflection coefficients normalized to R, S characterizes the imaginary component of the interference of the two complex reflection coefficients normalized to R, and C characterizes the real component of the two complex reflection coefficients normalized to R. Thus, when the set of signal parameters is set to the third setting, in the regression corresponding to regression data object 720, which is linked to option data object 722, a combination of R, NSC of the measured diffraction signal and the one or more simulated diffraction signals is calculated and compared. In the present example, the third setting of the set of signal parameters can correspond to a spectroscopic ellipsometer.

It should be recognized, however, that option data object 722 can include any number of signal parameters. It should also be recognized that various settings of the set of signal parameter can correspond to various types, brands, and/or models of optical metrology tools.

Metric data object 724 is linked to profile model data object 712. Metric data object 724 includes one or more profile parameters to be provided to the user in examining the structure. For example, metric data object 724 can include the bottom CD of a profile model. Thus, while the profile model can be defined using multiple profile parameters, only the bottom CD is provided to the user.

A fifth level of the hierarchy of project data structure 700 includes a simulation data object 716 linked to noise data object 718 and option data object 722. Simulation data object 716 includes a simulated diffraction signal generated for a particular profile model using a numerical analysis technique, such as RCWA, or a MLS. In generating the simulated diffraction signal, the data related to noise measurements in noise data object 718 can be used. Also, as described above, the settings of the signal parameters in option data object 722 can be used in generating the simulated diffraction signal.

Regression data object 720 is linked to option data object 722. As described above, in a regression-based process, a measured diffraction signal of a structure can be compared to one simulated diffraction signal generated using a hypothetical profile. If the diffraction signals do not match within a matching criterion, the measured diffraction signal can be compared to another simulated diffraction signal generated using another hypothetical profile. In one exemplary embodiment, a quick local search, such as a gradient method or simulated annealing method, is performed. In the present exemplary embodiment, a set of measured diffraction signals, which can include hundreds or thousands of measured diffraction signals, is obtained. Regressions are performed using the set of measured diffraction signals. The results of the regressions, including the simulated diffraction signals that were found to adequately match the measured diffraction signals, are stored in regression data object 720.

Test profile model data object 714 is linked to option data object 722 and processed-data data object 706. As described above, option data object 722 is linked to profile model data object 712 and wavelength data object 708. Thus, for the current version of the profile model of the structure stored in profile model data object 712 and based on the data stored in the data objects to which test profile model data object 714 is connected in project data structure 700 (e.g., processed-data data object 706, option data object 722, wavelength data object 708, etc.), a more limited regression is performed than the regression performed corresponding to regression data object 720. For example, a single measured diffraction signal is used rather than a set of measured diffraction signals to perform the regression corresponding to test profile model data object 714. The results of the regression, including the simulated diffraction signal that was found to adequately match the measured diffraction signal, are stored in test profile model data object 714.

A sixth level of the hierarchy of project data structure 700 includes a library data object 726 linked to regression data object 720. As described above, the profile parameters that define a profile model can be varied to generate hypothetical profiles of varying shapes and dimensions. Simulated diffraction signals are generated for the hypothetical profiles. The simulated diffraction signals and the corresponding hypothetical profiles are stored in a library. In the present exemplary embodiment, the library is stored in library data object 726.

A seventh level of the hierarchy of project data structure 700 includes a tool-to-tool matching data object 730 linked to processed-data data object 706. A set of signal adjustment vectors can be generated to enable measurements obtained from one optical metrology tool to be used with measurements obtained from another optical metrology tool. For example, a set of sites on a wafer can be measured with a first metrology device and a second metrology device. Differences between signals of the first set of diffraction signals and the corresponding signals of the second sets of diffraction signals are calculated to determine the signal adjustment vectors. The set of signal adjustment vectors can be stored in tool-to-tool matching data object 730. For a more detailed description of generating signal adjustment vectors, see U.S. Pat. No. 6,792,328, issued on Sep. 14, 2004, which is incorporated herein by reference in its entirety.

A library verification data object 728 is linked to option data object 722. Library verification data object 728 is also linked to library data object 726 and processed-data data object 706. A generated library can be verified by obtaining a set of measured diffraction signals. The set of measured diffraction signals is compared to the simulated diffraction signals in the generated library to determine best matching diffraction signals. In the present exemplary embodiment, results of the verification process are stored in library verification data object 728.

A spectra simulation data object 732 is linked to wavelength data object 708. Spectra simulation data object 732 is also linked to profile model data object 712 and processed-data data object 706. In the present exemplary embodiment, one or more profile parameters of a profile model are varied, then sets of simulated diffraction signals are generated to evaluate the effects of varying the one or more profile parameters on the generated simulated diffraction signals. For example, assume a profile model is defined using profile parameters X0, X1, and X2. Assume X1 and X2 are set to fixed values, while X0 is varied over a range of values. For each value of X0, a simulated diffraction signal is generated. X0 and X2 can then be set to fixed values, while X1 is varied over a range of values. For each value of X1, a simulated diffraction signal is generated. X0 and X1 can then be set to fixed values, while X2 is varied over a range of values. For each value of X2, a simulated diffraction signal is generated. The sets of simulated diffraction signals are plotted on top of each other and displayed to a user. The sets of simulated diffraction signals are stored in spectra simulation data object 732. In generating the sets of simulated diffraction signals, it should be recognized that any number of profile parameters can be set to fixed values, while any number of profile parameters are varied over ranges of values.

Project data structure 700 has been described above as being organized using a hierarchical scheme. It should be recognized, however, that project data structure 700 can be organized using various organizational schemes, such as network, relational, object-relational, object-oriented, associative, context, entry-attribute-value models, and the like.

As described above, in process 600 (FIG. 6), multiple settings of the signal parameters can be created and stored in option data objects. With reference to FIG. 8, project data structure 700 is depicted with multiple option data objects 722. It should be recognized that only a portion of project data structure 700 is depicted in FIG. 8 for the sake of clarity. Thus, project data structure 700 depicted in FIG. 8 can include the portions of project data structure 700 depicted in FIG. 7 and described above.

For the sake of example, FIG. 8 depicts four different option data objects 722. As depicted in FIG. 8, each option data object 722 has different settings of the set of signal parameters. For example, assume each option data object 722 includes signal parameters P0, P1, P2, and P3. Assume the first version of option data object 722 (identified in FIG. 8 as version 1.0) has signal parameter P0 set to be ON and signal parameters P1, P2, and P3 set to be OFF. Assume the second version of option data object 722 (identified in FIG. 8 as version 2.0) has signal parameter P1 set to be ON and signal parameters P0, P2, and P3 set to be OFF. Assume the third version of option data object 722 (identified in FIG. 8 as version 3.0) has signal parameter P2 set to be ON and signal parameters P0, P1, and P3 set to be OFF. Assume the fourth version of option data object 722 (identified in FIG. 8 as version 4.0) has signal parameter P3 set to be ON and signal parameters P0, P1, and P2 set to be OFF. It should be recognized that any number of different option data objects 722 can be created, and each option data object 722 can have any number of signal parameters.

As depicted in FIG. 8, in the present exemplary embodiment, each option data object 722 is linked with wavelength data object 708, which is linked with project data object 702. Furthermore, each option data object 722 is also linked with profile model data object 712, which in turn is linked with material data object 710, which is further linked with project data object 702.

In one exemplary embodiment, option data objects 722 can be marked and/or unmarked to be displayed or not displayed. In particular, if an option data object 722 is marked, then the marked option data object 722 is displayed. If an option data object 722 is unmarked, then the unmarked option data object 722 is not displayed. In one preferred embodiment, only one option data object 722 is displayed at a time. Thus, when one option data object 722 is marked to be displayed, all remaining option data objects 722 are unmarked and not displayed.

In one exemplary embodiment, a simulated diffraction signal is generated using the setting of the signal parameters specified in an option data object 722. For example, a simulated diffraction signal can be generated using a first version of option data object 722 (identified in FIG. 8 as version 1.0). Assume when the signal parameters are set as specified in the first version of option data object 722, measured and/or simulated diffraction signals are processed by calculating average reflectivity ($R_s$ and $R_p$). Thus, in the present example, average reflectivity ($R_s$ and $R_p$) is calculated in generating the simulated diffraction signal. The generated simulated diffraction signal is stored in simulation data object 716, which is linked with the first version of option data object 722. Another simulated diffraction signal can be generated using a second version of the option data object 722 (identified in FIG. 8 as version 2.0). Assume when the signal parameter are set as specified in the second version of option data object 722, measured and/or simulated diffraction signals are processed by calculating average of the difference of the s and p reflectivity $(R_s-R_p)/2$. Thus, in the present example, average of the difference of the s and p reflectivity $(R_s-R_p)/2$ is calculated in generating the simulated diffraction signal. The generated simulated diffraction signal is stored in another simulation data object 716, which is linked with the second version of option data object 722.

As depicted in FIG. 8, when multiple simulation data objects 716 are created, each simulation data object 716 is identified using a version number. For example, in FIG. 8, the first version of simulation data object 716 is identified as version 1.0, and the second version of simulation data object 716 is identified as version 2.0. Simulation data objects 716, the links between simulation data objects 716 and option data objects 722, and the version numbers associated with simulation data objects 716 are stored. As also depicted in FIG. 8, option data objects 722 are ultimately linked to project data object 702. Thus, a user can retrieve project data object 702 and access results of the previously performed simulations and the settings of the signal parameters that were used to perform the simulations.

It should be recognized that any number of simulations can be performed using one version of option data object 722. For example, a third simulation can be performed using the second version of option data object 722. Thus, in this example, the third simulation, which can be identified using a version number, is linked to the second version of option data object 722.

In one exemplary embodiment, a regression can be performed using the setting of the signal parameters specified in an option data object 722. For example, a regression can be performed using a third version of option data object 722 (identified in FIG. 8 as version 3.0). Assume when the signal parameters are set as specified in the third version of option data object 722, measured and/or simulated diffraction signals are processed by calculating a first combination of R, NSC. Thus, in the present example, in performing the regression, the first combination of R, NSC of the measured and simulated diffraction signals are calculated and compared. The results of the regression are stored in regression data object 720, which is linked with the third version of option data object 722. Another regression can be performed using a fourth version of option data object 722 (identified in FIG. 8 as version 4.0). Assume when the signal parameters are set as specified in the fourth version of option data object 722, measured and/or simulated diffraction signals are processed by calculating a second combination of R, NSC, where the second combination is different than the first combination used in conjunction with the third version of option data object 722. Thus, in the present example, in performing the regression, the second combination of R, NSC of the measured and simulated diffraction signals are calculated and compared. The results of the regression are stored in another regression data object 720, which is linked with the fourth version of option data object 722.

As depicted in FIG. 8, when multiple regression data objects 720 are created, each regression data object 720 is identified using a version number. For example, in FIG. 8, the first version of regression data object 720 is identified as version 1.0, and the second version of regression data object 720 is identified as version 2.0. Regression data objects 720, the links between regression data objects 720 and option data objects 722, and the version numbers associated with regression data objects 720 are stored. As also depicted in FIG. 8, option data objects 722 are ultimately linked to project data object 702. Thus, a user can retrieve project data object 702 and access results of the previously performed regressions and the settings of the signal parameters that were used to perform the regressions.

It should be recognized that any number of regressions can be performed using one version of option data object 722. For example, a third regression can be performed using the fourth version of option data object 722. Thus, in this example, the third regression, which can be identified using a version number, is linked to the fourth version of option data object 722.

In the present exemplary embodiment, a library of simulated diffraction signals and hypothetical profile can be generated using the setting of the signal parameters specified in an option data object 722. For example, a library can be generated using the third version of option data object 722 (identified in FIG. 8 as version 3.0). Assume again that when the signal parameters are set as specified in the third version of option data object 722, measured and/or simulated diffraction signals are processed by calculating a first combination of R, NSC. Thus, in the present example, the first combination of R, NSC is calculated in generating simulated diffraction signals for the library. The generated library is stored in library data object 726, which is linked with the third version of option data object 722. Another library can be generated using the fourth version of option data object 722 (identified in FIG. 8 as version 4.0). Assume when the signal parameters are set as specified in the fourth version of option data object 722, measured and/or simulated diffraction signals are processed by calculating a second combination of R, NSC, where the second combination is different than the first combination used in conjunction with the third version of option data object 722. Thus, in the present example, the second combination of R, NSC is calculated in generating simulated diffraction signals for the library. The library is stored in another library data object 726, which is linked with the fourth version of option data object 722.

As depicted in FIG. 8, when multiple library data objects 726 are created, each library data object 726 is identified using a version number. For example, in FIG. 8, the first version of library data object 726 is identified as version 1.0, and the second version of library data object 726 is identified as version 2.0. Library data objects 726, the links between library data objects 726 and option data objects 722, including any intermediate links, and the version numbers associated with library data objects 726 are stored. As also depicted in FIG. 8, option data objects 722 are ultimately linked to project data object 702. Thus, a user can retrieve project data object 702 and access the previously generated libraries and the settings of the signal parameters that were used to generate the libraries.

It should be recognized that any number of libraries can be generated using one version of option data object 722. For example, a third library can be generated using the fourth version of option data object 722. Thus, in this example, the third library, which can be identified using a version number, is linked to fourth version of option data object 722.

In the present exemplary embodiment, after a library has been generated, one or more verification processes can be performed to verify the library. As described above, a generated library can be verified by obtaining a set of measured diffraction signals. The set of measured diffraction signals is compared to the simulated diffraction signals in the generated library to determine best matching diffraction signals. The measured and simulated diffraction signals are compared based on the settings of the signal parameters in the option data object 722. Results of the verification process are stored in verify library verification data object 728.

For example, a verification process can be performed on the library generated using the third version of option data object 722 (identified in FIG. 8 as version 3.0). Assume again that when the signal parameters are set as specified in the third version of option data object 722, measured and/or simulated diffraction signals are processed by calculating a first combination of R, NSC. Thus, in the present example, in performing the verification process, the first combination of R, NSC of the measured and simulated diffraction signals are calculated and compared. The results of the verification process are stored in library verification data object 728, which is linked with the third version of option data object 722. Another verification process can be performed on the library using the fourth version of option data object 722 (identified in FIG. 8 as version 4.0). Assume when the signal parameters are set as specified in the fourth version of option data object 722, measured and/or simulated diffraction signals are processed by calculating a second combination of R, NSC, where the second combination is different than the first combination used in conjunction with the third version of option data object 722. Thus, in the present example, in performing the regression, the second combination of R, NSC of the measured and simulated diffraction signals are calculated and compared. The results of the verification process are stored in another library verification data object 728, which is linked with the fourth version of option data object 722.

As depicted in FIG. 8, when multiple library verification data objects 728 are created, each library verification data object 728 is identified using a version number. For example, in FIG. 8, the first version of library verification data object 728 is identified as version 1.0, and the second version of library verification data object 728 is identified as version 2.0. Library verification data objects 728, the links between library verification data objects 728 and option data objects 722, including any intermediate links, and the version numbers associated with library verification data objects 728 are stored. As also depicted in FIG. 8, option data objects 722 are ultimately linked to project data object 702. Thus, a user can retrieve project data object 702 and access the results of the previously performed verification processes, the previously generated libraries, and the settings of the signal parameters that were used to verify the libraries.

It should be recognized that any number of library verification processes can be performed using one version of data object 722. For example, a third library verification process can be performed using the fourth version of option data object 722. Thus, in this example, the results of the third library verification process, which can be identified using a version number, is linked to library data object 726, which is linked to the fourth version of option data object 722.

As described above, in one exemplary embodiment, option data objects 722 can be marked and/or unmarked to be displayed or not displayed. In this embodiment, if an option data object 722 is marked and displayed, then any data object in the hierarchy below the marked option data object 713 and linked to the marked option data object 722 is displayed. For example, if option data object 722 associated with the third version of option data object 722 is marked and displayed, then the first version of regression data object 720, the first version of library data object 726, and the first version of library verification data object 728 are displayed.

In one exemplary embodiment, the data in project data structure 700 is stored by grouping different types of data together. FIG. 9 is an exemplary class diagram depicting how data in project data structure 700 (FIG. 7) is stored. In the present exemplary embodiment, the various types of data objects of project data structure 700 (FIG. 7) are stored together in a serial data object list 908. The links between the data objects of project data structure 700 (FIG. 7) are stored together in an object data map list 910. The names of the data object, object identification, and other application internal information, are stored together in a data object list 912. Identification of the data objects of project data structure 700 (FIG. 7) as different types of data objects is stored in a data object information 914. In the present exemplary embodiment, serial data object list 908 and object data map list 910 are hash tables. It should be recognized, however, that data in project data structure 700 (FIG. 7) can be stored using various formats.

As depicted in FIG. 9, in the present exemplary embodiment, an object manager 902 includes a primary project data structure 904 and a secondary project data structure 906. Primary project data structure 904 and secondary project data structure 906 can be separate project data structures, such as project data structure 700 (FIG. 7), to allow a user to access two project data structures at the same time. Alternatively, data from secondary project data structure 906 can be used in primary project data structure 904, or vice versa.

For example, secondary project data structure 906 can relate to a project data structure for profile models of a thin film structure. Primary project data structure 904 can relate to a project data structure for profile models of a patterned structure that is formed on the thin film structure. Thus, the profile models and/or libraries of secondary project data structure 906 can be used in primary project data structure 904. As a further example, a library generated in secondary project data structure 906 can be used to determine the thickness of an underlying layer of a patterned structure. The determined thickness can be used to fix the value of the corresponding layer in generating or using a library in primary project data structure 904 for the patterned structure.

With reference to FIG. 10, exemplary operations of an object manager are depicted. In particular, in operation 1002, an instance of the object manager is activated. In operation 1004, a new project data structure is created. In operation 1006, a previously saved project data structure is loaded. In operation 1008, a project data structure is deleted.

With continued reference to FIG. 10, when a new project data structure is created, in operation 1010, a new data object can be added. In operation 1012, an existing data object can be updated. In operation 1014, a data object can be deleted. In operation 1016, a data object can be saved. In operation 1018, a data object can be selected.

With reference to FIG. 11, in the present exemplary embodiment, the object manager can be run on a computer system 1100. As depicted in FIG. 11, computer system 1100 can include a processor 1102 that is configured to perform process 600 (FIG. 6) and the operations depicted in FIG. 10. Computer system 1100 can also include a computer-readable medium 1104, such as a hard disk, solid state memory, etc., that can include computer-executable instructions to direct the operation of processor 1102 in performing process 600 (FIG. 6) and the operations depicted in FIG. 10. Computer-readable medium 1104 can also store a project data structure, such as project data structure 700 (FIGS. 7 and 8). Computer system 1100 can further include an input device 1106 configured to receive input from the user and a display screen 1108.

It should be recognized that computer system 1100 can include various additional components not depicted in FIG. 11. Additionally, it should be recognized that computer system 1000 can be physically embodied in various forms. For example, computer system 1100 can be a unitary computer, such as a workstation, or can be part of a distributed computer system.

Although exemplary embodiments have been described, various modifications can be made without departing from the spirit and/or scope of the present invention. Therefore, the present invention should not be construed as being limited to the specific forms shown in the drawings and described above.

We claim:

1. A method of managing data flow in generating different signal formats for use in optical metrology, the method comprising:
    creating a project data object;
    creating a first option data object having a set of signal parameters, wherein different settings of the set of signal parameters correspond to different signal formats for diffraction signals;
    associating a version number with the first option data object;
    linking the first option data object with the project data object;
    creating at least a second option data object having a set of signal parameters, wherein different settings of the set of signal parameters correspond to different signal formats for diffraction signals, wherein the set of signal parameters of the first option data object and the set of signal parameters of the second option data object are set differently;
    associating another version number with the second option data object;
    linking the second option data object with the project data object;
    storing the project data object, the first option data object, and the second option data object;
    storing the version numbers associated with the first option data object and the second option data object;
    storing the link between the first option data object and the project data object; and
    storing the link between the second option data object and the project data object.

2. The method of claim 1, wherein different settings of the set of signal parameters of the first option data object or the second option data object correspond to different types, brands, and/or models of optical metrology tools.

3. The method of claim 1, further comprising:
    marking the first option data object and unmarking the second option data object to display the first option data object and not display the second option data object; or
    marking the second option data object and unmarking the first option data object to display the second option data object and not display the first option data object.

4. The method of claim 1, further comprising:
    performing a first regression using the setting of the set of signal parameters of the first option data object to obtain results of the first regression;
    storing the results of the first regression in a first regression data object;
    linking the first regression data object with the first option data object; and
    storing the link between the first regression data object and the first option data object.

5. The method of claim 4, further comprising:
    performing a second regression using the setting of the set of signal parameters of the second option data object to obtain results of the second regression;
    storing the results of the second regression in a second regression data object;
    associating version numbers with the first and second regression data objects;
    linking the second regression data object with the second option data object;
    storing the version numbers associated with the first and second regression data objects; and
    storing the link between the second regression data object and the second option data object.

6. The method of claim 1, further comprising:
    performing a first simulation using the setting of the set of signal parameters of the first option data object to obtain a first simulated diffraction signal;
    storing the first simulated diffraction signal in a first simulation data object;
    linking the first simulation data object with the first option data object; and
    storing the link between the first simulation data object and the first option data object.

7. The method of claim 6, further comprising:
    performing a second simulation using the setting of the set of signal parameters of the second option data object to obtain a second simulated diffraction signal;
    storing the second simulated diffraction signal in a second simulation data object;
    associating version numbers with the first and second simulation data objects;
    linking the second simulation data object with the second option data object;
    storing the version numbers associated with the first and second simulation data objects; and
    storing the link between the second simulation data object and the second option data object.

8. The method of claim 1, further comprising:
    generating a first library of simulated diffraction signals and hypothetical profiles using setting of the set of signal parameters of the first option data object;
    storing the first library in a first library data object;
    linking the first library data object with the first option data object; and
    storing the link between the first library data object and the first option data object.

9. The method of claim 8, further comprising
generating a second library of simulated diffraction signals and hypothetical profiles using the setting of the set of signal parameters of the second option data object;
storing the second library in a second library data object;
associating version numbers with the first and second library data objects;
linking the second library data object with the second option data object;
storing the version numbers associated with the first and second library data objects; and
storing the link between the second library data object and the second option data object.

10. The method of claim 8, further comprising:
generating a third library of simulated diffraction signals and hypothetical profiles using the setting of the set of signal parameters of the first option data object;
storing the third library in a third library data object;
associating version numbers with the first and third library data objects;
linking the third library data object with the first option data object;
storing the version numbers associated with the first and third library data objects; and
storing the link between the third library data object and the first option data object.

11. The method of claim 8, further comprising:
verifying the first library using the setting of the set of signal parameters of the first option data object;
storing results of the verification of the first library in a first library verification data object;
linking first library verification data object with the first option data object; and
storing the link between the first library verification data object and the first option data object.

12. The method of claim 11, further comprising:
verifying a second library using the setting of the set of signal parameters of the second option data object;
storing results of the verification of the second library in a second library verification data object;
associating version numbers with the first and second library verification data objects;
linking second library verification data object with the second option data object;
storing the verification numbers associated with the first and second library verification data objects; and
storing the link between the second library verification data object and the second option data object.

13. The method of claim 1, further comprising:
creating a material data object, the material data object including optical constants n and k;
linking the material data object to the project data object;
linking the material data object to the first option data object, wherein the material data object is linked between the project data object and the first option data object;
linking the material data object to the second option data object, wherein the material data object is linked between the project data object and the second option data object;
storing the material data object; and
storing the links amongst the material data object, the project data object, the first option data object, and the second option data object.

14. The method of claim 13, further comprising:
creating a raw-data data object associated with measurements obtained from one or more optical metrology tools;
creating a wavelength data object associated with wavelengths to be used in obtaining measurements from the one or more optical metrology tools;
creating a processed-data data object associated with adjusted measurements obtained from the one or more optical metrology tools;
linking the raw-data data object, the processed-data data object, and the wavelength data object with the project data object;
storing the raw-data data object, the processed-data data object, and the wavelength data object; and
storing the links amongst the raw-data data object, the processed-data data object, the wavelength data object, and the project data object.

15. The method of claim 14, wherein the project data object, the material data object, the first option data object, the second option data object, the raw-data data object, the wavelength data object, and the processed-data data object are arranged in a hierarchy, wherein changes to data objects higher in the hierarchy result in changes to linked data objects lower in the hierarchy, and wherein changes to data object lower in the hierarchy do not necessarily result in changes to linked data objects higher in the hierarchy.

16. A computer-readable storage medium containing computer-executable instructions for managing data flow in generating different signal formats for use in optical metrology, comprising instructions for:
creating a project data object;
creating a first option data object having a set of signal parameters, wherein different settings of the set of signal parameters correspond to different signal formats for diffraction signals;
associating a version number with the first option data object;
linking the first option data object with the project data object;
creating at least a second option data object having a set of signal parameters, wherein different settings of the set of signal parameters correspond to different signal formats for diffraction signals, wherein the set of signal parameters of the first option data object and the set of signal parameters of the second option data object are set differently;
associating another version number with the second option data object;
linking the second option data object with the project data object;
storing the project data object, the first option data object, and the second option data object;
storing the version numbers associated with the first option data object and the second option data object;
storing the link between the first option data object and the project data object; and
storing the link between the second option data object and the project data object.

17. A computer system for managing data flow in generating different signal formats for use in optical metrology, comprising:
a computer-readable storage medium configured to store a project data structure; and
a processor connected to the computer-readable storage medium, the processor configured to:
create a project data object;

create a first option data object having a set of signal parameters, wherein different settings of the set of signal parameters correspond to different signal formats for diffraction signals;

associate a version number with the first option data object;

link the first option data object with the project data object;

create at least a second option data object having a set of signal parameters, wherein different settings of the set of signal parameters correspond to different signal formats for diffraction signals, wherein the set of signal parameters of the first option data object and the set of signal parameters of the second option data object are set differently;

associate another version number with the second option data object;

link the second option data object with the project data object;

store the project data object, the first option data object, and the second option data object as part of the project data structure stored on the computer-readable storage medium;

store the version numbers associated with the first option data object and the second option data object as part of the project data structure stored on the computer-readable storage medium;

store the link between the first option data object and the project data object as part of the project data structure stored on the computer-readable storage medium; and store the link between the second option data object and the project data object as part of the project data structure stored on the computer-readable storage medium.

18. The computer system of claim 17, further comprising:
a display screen connected to the processor, wherein the processor is configured to:
mark the first option data object and unmark the second option data object to display the first option data object on the display screen and not display the second option data object; or
mark the second option data object and unmark the first option data object to display the second option data object on the display screen and not display the first option data object.

19. The computer system of claim 17, wherein the processor is configured to:
generate a first library of simulated diffraction signals and hypothetical profiles using setting of the set of signal parameters of the first option data object;
store the first library in a first library data object as part of the project data structure stored on the computer-readable medium;
link the first library data object with the first option data object; and
store the link between the first library data object and the first option data object as part of the project data structure stored on the computer-readable medium.

20. The computer system of claim 19, wherein the processor is configured to:
generate a second library of simulated diffraction signals and hypothetical profiles using the setting of the set of signal parameters of the second option data object;
store the second library in a second library data object as part of the project data structure stored on the computer-readable medium;

associate version numbers with the first and second library data objects;
link the second library data object with the second option data object;
store the version numbers associated with the first and second library data objects as part of the project data structure stored on the computer-readable medium; and
store the link between the second library data object and the second option data object as part of the project data structure stored on the computer-readable medium.

21. The computer system of claim 19, wherein the processor is configured to:
generate a third library of simulated diffraction signals and hypothetical profiles using the setting of the set of signal parameters of the first option data object;
store the third library in a third library data object as part of the project data structure stored on the computer-readable medium;
associate version numbers with the first and third library data objects;
link the third library data object with the first option data object;
store the version numbers associated with the first and third library data objects; and
store the link between the third library data object and the first option data object as part of the project data structure stored on the computer-readable medium.

22. A method of organizing data objects for generating and using libraries for use in optical metrology, the method comprising:
creating a project data object;
creating a first option data object having a set of signal parameters, wherein different settings of the set of signal parameters correspond to different signal formats for diffraction signals;
associating a version number with the first option data object;
linking the first option data object with the project data object;
creating at least a second option data object having a set of signal parameters, wherein different settings of the set of signal parameters correspond to different signal formats for diffraction signals, wherein the set of signal parameters of the first option data object and the set of signal parameters of the second option data object are set differently;
associating another version number with the second option data object;
linking the second option data object with the project data object;
storing the project data object, the first option data object, and the second option data object;
storing the version numbers associated with the first option data object and the second option data object;
storing the link between the first option data object and the project data object;
storing the link between the second option data object and the project data object,
creating a wavelength data object;
creating a material data object; and
creating a profile model data object corresponding to a profile model.

23. The method of claim 22 further comprising:
performing a regression using the profile model and the signal format corresponding to the setting of the set of signal parameters in the first option data object.

24. The method of claim 22 further comprising:
performing a simulation using the profile model and the signal format corresponding to the setting of the set of signal parameters in the first option data object.

25. The method of claim 22 further comprising:
generating a library of simulated diffraction signals and hypothetical profiles using the profile model and the signal format corresponding to the setting of the set of signal parameters in the first option data object.

26. The method of claim 25 further comprising:
verifying the library of simulated diffraction signals and hypothetical profiles using the signal format corresponding to the setting of the set of signal parameters in the first option data object.

* * * * *